United States Patent [19]
Carlson et al.

[11] Patent Number: 4,912,270
[45] Date of Patent: Mar. 27, 1990

[54] CHROMIA AEROGEL, METHOD OF PRODUCING SAME AND FLUORINATION PROCESS UTILIZING SAME

[75] Inventors: Emery J. Carlson, Chatham; John N. Armor, Morris Plains, both of N.J.; William J. Cunningham, Williamsville; Addison M. Smith, Amherst, both of N.Y.

[73] Assignee: Allied-Signal Inc., Morris Township, Morris County, N.J.

[21] Appl. No.: 282,545

[22] Filed: Dec. 12, 1988

Related U.S. Application Data

[60] Division of Ser. No. 124,372, Nov. 23, 1987, Pat. No. 4,828,818, which is a continuation of Ser. No. 27,093, Mar. 13, 1987, abandoned, which is a continuation of Ser. No. 763,505, Aug. 8, 1985, abandoned.

[51] Int. Cl.[4] .............................................. C07C 17/20
[52] U.S. Cl. ..................................... 570/169; 570/165
[58] Field of Search ................................. 570/165, 169

[56] References Cited

U.S. PATENT DOCUMENTS 3,258,500  6/1966  Swamer et al. ...................... 570/169
4,828,818  5/1989  Carlson et al. ...................... 423/607

OTHER PUBLICATIONS

Burwell, Jr. et al., *Am. Chem. Soc.*, vol. 82, pp. 6272-6291 (1960).

Primary Examiner—Alan Siegel
Attorney, Agent, or Firm—Ernest D. Buff; Gerhard H. Fuchs; Richard C. Stewart

[57] ABSTRACT

Chromium(III) oxide and hydroxide aerogels are produced by the reaction of chromium(VI) oxide with a solvent which is reducing to chromium(VI), such as methanol, heating the solution to hypercritical conditions, and venting the solvent hypercritically. The product aerogels exhibit surface areas above 400 m$^2$/g, pore volumes of at least 2 cm$^3$/g and a substantially uniform pore size distribution. Also disclosed is a unique process which employs high pore volume, high surface area chromium(III) oxide or hydroxide as a fluorination catalyst. More particularly, reaction of $C_2Cl_3F_3$ with HF over these catalysts produced high yields of $C_2Cl_2F_4$ and $C_2ClF_5$.

3 Claims, No Drawings

CHROMIA AEROGEL, METHOD OF PRODUCING SAME AND FLUORINATION PROCESS UTILIZING SAME

This application is a division of application Ser. No. 124,372 filed 11/23/87 now U.S. Pat. No. 4,828,818 which in lieu is a continuation of Ser. No. 027,093, filed Nov. 13, 1987 now abandoned, which in turn is a continuation of Ser. No. 763,505, filed Aug. 8, 1985 now abandoned.

BACKGROUND OF THE INVENTION

The present invention relates to high surface area chromium oxides and hydroxides of valence state III useful as catalysts for a variety of processes including fluorination.

Aerogels of various metal oxides have been prepared by hydrolysis of alkoxides of silicon, aluminum, magnesium, and certain other metals whose alkoxides are soluble in lower alcohols, followed by hypercritical removal of solvent. Chromium(III) does not have readily available alkoxides suitable for this use. Nevertheless, chromium(III) oxide and hydroxide (generally referred to as chromia) are used for variety of catalytic processes where increased surface area might improve activity. Available chromia catalysts generally have surface areas (by the BET technique) no greater than 350 $m^2/g$ and frequently less than 250 $m^2/g$. See, for example, R. L. Burwell Jr. et al., Am. Chem. Soc. 58, 697 (1936), and R. L. Burwell Jr. et al., Am. Chem. Soc. 82, 6272 (1960).

Chromium(III) oxide catalysts for the fluorination of chlorinated hydrocarbons by HF are disclosed in U.S. Pat. Nos. 3,258,500 (to Swamer et al.) and 3,978,145 (to Knaak). The former discloses a preferred gel-type catalyst produced by reducing chromium(VI) oxide with ethanol in water, drying the gel and activating in an inert atmosphere at 400–600° C. The latter discloses a chromium(III) oxide gel-type catalyst hydrated with water at elevated temperatures before use.

BRIEF DESCRIPTION OF THE INVENTION

The present invention includes a method for preparing a chromium oxide or hydroxide aerogel which comprises the steps of:
 (a) forming a solution comprising chromium(VI) oxide in a solvent which is reducing to chromium(VI) oxide
 (b) heating said solution to a temperature where said chromium(VI) oxide is reduced by said solvent to a solid oxide or hydroxide form, producing a slurry or gel;
 (c) continuing to heat said slurry or gel under pressure to above the critical temperature of the solvent; and,
 (d) venting said solvent and oxidation products thereof hypercritically to produce a chromium(III) oxide or hydroxide aerogel of surface area at least about 200 $m^2/g$.

The present invention also includes a chromium(III) oxide or hydroxide product, preferably produced by the novel process, which has a surface area of at least about 400 $m^2/g$, a pore volume of at least about 2 $cm^3/g$ and a substantially uniform pore size distribution (by mercury porosimetry). The present invention also includes an improved process for the fluorination of a halogenated hydrocarbon having at least one chlorine atom by reacting said halogenated hydrocarbon with HF in the presence of chromium(III) oxide or hydroxide catalysts. In this improved fluorination process, the catalyst is the improved chromium(III) oxide or hydroxide aerogel of the present invention, and preferably is the product of the preferred method of making chromium oxide or hydroxide aerogels.

DETAILED DESCRIPTION OF THE INVENTION

The method involving steps a–d (recited above) is a novel and the preferred, but not the exclusive, method to produce a product which is particularly useful as a catalyst in hydrocarbon fluorination processes.

The first step of the method involves forming a solution. Chromium(VI) oxide of any quality or phase structure, and which may include common impurities, is used to form the solution. In addition, the chromium (VI) oxide may exist in its anhydrous or hydrated form, such as chromic acid. To form the solution, any solvent which is reducing to chromium(VI) may be employed. For example, acetone, alcohol, and typical hydrocarbon solvents such as toluene may be used. The solvent preferably includes at least one aliphatic alcohol of 1–4 carbons such as methanol, ethanol, isopropanol, n-propanol, n-butanol, i-butanol, or t-butanol, with methanol being most preferred. More preferably, the solvent is one of these aliphatic alcohols. Moreover, the most preferred solvent is methanol. Additional components, and especially water, may be present if the chromium(VI) oxide is soluble in the solvent and should be present if the chromium(VI) oxide is not soluble in the reducing solvent to the desired extent.

The concentration of chromium(VI) oxide in solution and the initial-forming temperature are not critical, but for the reason discussed below, it is preferred to have a chromium(VI) oxide concentration in solution below about 70 g/l and more preferably below about 40–50 g/l, before permitting the solution temperature to exceed about 40° C. A preferred solution-forming technique is to use at least about 3 parts by weight of water per part by weight of chromium(VI) oxide, to combine about one-third to about one-half of the water with the oxide (to form a solution A), to combine the remaining water with the solvent (to form a solution B), and finally, to gradually add solution A to solution B.

On heating, the chromium(VI) oxide reacts with the solvent to produce chromium(III) oxide or hydroxide and by-products (principally carbon monoxide or carbon dioxide, formaldehyde, or formic acid when the solvent is methanol). Because the reaction of solvent (and especially alcohol) with chromium(VI) oxide is very exothermic, it is preferred to have this reaction occur at relatively low chromium(VI) oxide concentrations (and preferably at the concentration noted above). Moreover, water, in addition to its function as a co-solvent for some systems, is preferably present to function to absorb the heat of reaction. THe reaction product ordinarily exists as a gel comprising the chromium(III) oxide or hydroxide precipitate rather than as a precipitate separated from a solution.

Heating is continued to at least about, and preferably above, the critical temperature of the solvent (i.e., the remaining reducing solvent and other constituents, such as water). Thereafter, the solvent (which also includes oxidation products) is vented hypercritically (i.e., at or above the critical temperature). The critical temperature of, for example, a 90/10 methanol- to-water solvent system is about 260° C., and for about a 80/20 methanol-to-water solvent system is about 280° C. Any residual solvent can then be removed by vacuum drying or heating under, for example, an inert atmosphere. However, this is generally not required because we normally purge the system using dry nitrogen gas at a temperature of above about 250° C.

The product produced by the process will have a surface area of at least about 200 m$^2$/g by the BET technique, preferably at least about 400 m$^2$/g, and more preferably between about 500 m$^2$/g and about 800 m$^2$/g. Moreover, the product will also exhibit a pore volume of at least about 2 cm$^3$/g and a substantially uniform pore size distribution (i.e., no predominant pore size). The product will be substantially chromium(III) oxide or hydroxide which is either amorphous or of a conventional crystalline phase structure for chromium-(III) oxide. With this process, residual carbon, as surface alkoxide, is present, if at all, only in trace amounts (the weight ratio of carbon to chromium is at most about 1:1000). Consequently, the product (including the hydrogen proportion) can be represented by the formulae Cr(OH)$_3$, CrO(OH), mixtures thereof or mixtures of either or both with Cr$_2$O$_3$.

The catalytic process of the invention employs as catalyst either the direct product of the preferred method, a heat activated form thereof, a steam activated form thereof, forms thereof supported on an inert carrier or alternative forms of the present chromium(III) oxide or hydroxide aerogel not necessarily formed from chromium(VI) oxide but which exhibit the previously noted improved properties. For example, useful novel aerogel products may b prepared by a process which combines known gel forming techniques coupled with hypercritical venting, as illustrated in Example 2 hereinbelow. Other similar products may be prepared by the hypercritical venting of a solution of chromium(III) acetate or other chromium(III) salts such as hydroxy acetate, formate, acetyl-acetonate or carbonate. With either process, the desired product cation has a +3 valence, a surface area of at least about 400 m$^2$/g, preferably between about 500 and about 800 m$^2$/g, a pore volume of at least about 2 cm$^3$/g and a substantially uniform pore size distribution (by mercury porosimetry).

Suitable halogenated hydrocarbons for the catalytic process include CCl$_4$, CCl$_3$F, CCl$_2$F$_2$, CClF$_3$, C$_2$Cl$_6$, C$_2$Cl$_4$, C$_2$Cl$_5$F, C$_2$Cl$_4$F$_2$, C$_2$Cl$_3$F$_3$, C$_2$Cl$_2$F$_4$, C$_2$ClF$_5$ (including all isomers). Hydrohalocarbons such as C$_2$H$_2$Cl$_3$F, C$_2$HCl$_2$F$_3$ and CHClF$_2$ may also be used as reactants, but are less preferred. Preferred reactants include CCl$_3$F (fluorocarbon 11), CCl$_2$F$_2$ (fluorocarbon 12), C$_2$Cl$_3$F$_3$ (fluorocarbon 113) and C$_2$Cl$_2$F$_4$ (fluorocarbon 114). Preferred products include CClF$_3$ (fluorocarbon 13), CF$_4$ (fluorocarbon 14), C$_2$ClF$_5$ (fluorocarbon 115) and C$_2$F$_6$ (fluorocarbon 116). Exemplary processes include reaction of fluorocarbon 113 with HF to produce fluorocarbons 114, 115 and 116 in various proportions and reaction of fluorocarbon 12 with HF to produce fluorocarbon 14, with fluorocarbons 12 and 13 recycled.

The molar ratio of HX (where X is a halogen to reactant is not critical, and may be varied depending upon the reactant and desired product. For example, if HF is reacted with fluorocarbon 113, a 3:1 or larger molar ratio could be used if fluorocarbon 116 is the desired principal product, but a ratio of about 1:1-2:1 may be used if fluorocarbon 114 and 115 are the desired principal products. Contact time is generally not critical, but it is preferred that sufficient contact time be employed to provide an HF conversion of at least 40%, preferably at least 70%. Separation of the halocarbon products from any remaining HX, and separation of halocarbons from each other can e performed in a conventional fashion, e.g., by distillation and/or water scrubbing.

EXAMPLE 1

To a mixture of 105 mL methanol and 9 mL water was added (with stirring and very carefully, respecting the highly exothermic nature of the reaction) a solution of 4 g CrO$_3$ predissolved n 6 mL water. The clear, colored solution was placed in the glass liner of an autoclave, and the autoclave sealed. The mixture was heated gradually over 3 hours to above the calculated critical temperature of the methanol-water mixture (to about 285° C.). No temperature or pressure surges were observed, and the maximum pressure observed was 2350 psig (16.3 MPa). Shortly thereafter, the fluid phase was vented hypercritically, and the autoclave was subsequently purged with dry N$_2$. Upon cooling, an essentially uniform black, bulky, water-insoluble aerogel residue, somewhat chunky, with a deep green cast, was removed and portions analyzed. It had a surface area (BET, liquid nitrogen) of 609 m$^2$/g. Analysis by scanning mercury porosimetry (Quantachrome Corporation) u to a maximum pressure of 60,000 psig (44 MPa) indicated a pore volume of 3.3 cm$^3$/g, with broad, substantially uniform pore distribution ranging from large pores to small pores at the 39 Angstron diameter detection limit (based on the Kelvin equation and standard assumptions such as pore filling rather than pore collapse).

EXAMPLE 2

Urea (609) was dissolved in 4 L of a hot aqueous solution of chromium(III) nitrate (0.0375 mol/L). After several hours of hydrolysis at 96–99° C., a bulky gelatinous mass of chromic oxide-hydroxy salt precipitated. Rather than recovering this salt as a gel by filtration, washing and drying in the manner of Pass, Littlewood & Burwell, J. Am. Chem. Soc. 82, 6281–83 (1960), the excess liquid was decanted off, the gel (without allowing it to dry) was repeatedly washed with water to remove any residual nitrate salts and any other soluble impurities, and then the gel was washed at least six times with methanol to replace the water as the gel liquid. The methanol-containing gel (500 mL) was divided into several portions: portion A of 70 mL was placed in the annulus of a 300 cm$^3$ autoclave fitted with two glass liners and portion B of 00 mL diluted with 30 mL more methanol and placed in the core of the same autoclave. The autoclave was then purged with nitrogen and heated gradually to 305° C. under 1900 psig (13.2 MPa) (hypercritical conditions). After about 60 minutes at this temperature, the fluid phase was vented while maintaining the hypercritical conditions, and the autoclave was purged with dry N$_2$. The two cromia residues (about 3g total) were dried in a vacuum oven at 120° C. overnight. Both were dark green aerogels. Aerogel A had a bulk density of 0.054 g/cm$^3$ and a surface area of 661 m$^2$/g. Heating portions of each at 250° C. in air caused blackening, but apparent retention of surface area (668 m$^2$/g for B was measured). Heating portions of each at 450° C. in air caused blackening, obvious shrinkage and loss of measured surface area (114 m$^2$/g for B).

It should be appreciated that the procedure of Example 1 is less complex and utilizes cheaper and more readily available materials than the procedure of Example 2, while producing substantially the same aerogel product.

EXAMPLE 3—FLUORINATION CATALYST PRODUCTION

Following the general procedures of Example 1, 105 mL methanol, 9 mL water and a solution of 4 g chromic acid predissolved in 6 mL water were carefully combined and charged to a glass lined autoclave. The autoclave was then heated over several hours to 280° C and vented hypercritically (the peak pressure was =16.3 MPa). Upon cooling under nitrogen, a black, bulky, waterinsoluble residue was recovered which had a surface area by the BET technique of 609 m$^2$/g. Mercury porosimetry showed a surface area of 452 m$^2$/g, a pore volume of 3.3 cm$^3$/g, and no sudden changes in the slope of the curve representing the pore distribution in the product (up to a maximum pressure of 60,000 psig which represents pores of 39 Angstroms in diameter. Elemental analysis showed no carbon, 1.52% H and 59.10% Cr. This analysis can be represented by the formula $Cr_2O_{2.99}(H_2O)_{1.34}$.

EXAMPLE 4

The catalyst produced in Example 3 was used in a fluorination reaction. The reactor was a one-half inch (1.27 cm) inside diameter, 30 inch (76.2 cm) long Inconel ® pipe threaded and capped on both ends, fitted with an internally centered one-quarter inch (0.64 cm) outside diameter thermowell. The pipe was contained in a 24 inch (61 cm) long Lindberg furnace with three zones of independently controlled heating. HF was fed from a 40° C. cylinder through electrically heat-traced lines and a mass flow meter. Fluorocarbon 113 was fed by a pulsefeed pump into the HF line. The reactor was filled at the bottom (downstream) end with fluorinated alumina for the 3 inches (7.6 cm) extending below the furnace bottom and then by 100 mL (33.36 g) of compacted chromium(III) oxide/hydroxide aerogel of Example 3. During the heatup, nitrogen was fed through the reactor and 6.5 mol/h HF was also fed for two hours at 400° C to activate the catalyst (develop a "hot spot"). Then fluorocarbon 113 and HF were together fed into the reactor. The hot spot developed in each run during the first 30–60 minutes.

Samples were taken periodically from the exit gases for analysis of organics by gas chromatography. The remainder of the exit steam was passed through an empty tank (to accommodate any being drawn back), then to a water absorber, and finally through water-KOH scrubbers. Periodic analysis of the water absorber for total acid and chloride was used to determine HCl and HF in the product gases.

The fluorocarbon 113 feed rate was adjusted between 0.33 and 0.88 mol/h, while the HF feed rate was adjusted between 0.90 and 1.97 mol/h to give the indicated contact times (CT) and HF: fluorocarbon 113 mol ratios illustrated in Table 1 below.

TABLE 1

| Run | Furnace Temp.* | CT Sec | 113:HF Mol Ratio | Mol % Fluorocarbons** | | | | |
|-----|----------------|--------|------------------|-----|------|------|------|------|
|     |                |        |                  | 112 | 113  | 114  | 115  | 116  |
| 1   | 375° C.        | 4.42   | 2.33             | 0.36 | 4.48 | 34.7 | 57.6 | 2.88 |
| 2   | 375° C.        | 4.88   | 3.0              | 0.08 | 2.14 | 35.4 | 57.7 | 4.63 |
| 3   | 375° C.        | 2.56   | 2.94             | 0    | 2.04 | 54.0 | 42.0 | 1.96 |
| 4   | 375° C.        | 2.53   | 1.93             | 0.73 | 6.29 | 48.4 | 43.3 | 1.25 |

TABLE 1-continued

| Run | Furnace Temp.* | CT Sec | 113:HF Mol Ratio | Mol % Fluorocarbons** | | | | |
|-----|----------------|--------|------------------|-----|------|------|------|------|
|     |                |        |                  | 112 | 113  | 114  | 115  | 116  |
| 5   | 375° C.        | 4.48   | 2.36             | 0.20 | 2.80 | 40.4 | 53.7 | 2.91 |
| 6   | 375° C.        | 5.01   | 2                | 0.79 | 4.98 | 34.7 | 56.8 | 2.68 |
| 7   | 400° C.        | 4.86   | 2.05             | 0.52 | 5.23 | 23.3 | 66.5 | 4.44 |
| 8   | 400° C.        | 4.94   | 3                | 0    | 1.20 | 15.8 | 72.1 | 11.0 |
| 9   | 400° C.        | 2.52   | 2.92             | 0.12 | 1.88 | 30.1 | 62.5 | 5.42 |
| 10  | 400° C.        | 2.47   | 2                | 0.64 | 5.19 | 37.5 | 54.5 | 2.25 |
| 11  | 375° C.        | 4.42   | 2.4              | 0.25 | 3.11 | 42.0 | 52.1 | 2.53 |

*In each case where the reactor was at 375° C., a hot spot at about 390–395° C. was observed. In each case where the reactor was at 400° C., a hot spot at about 420–425° C. was observed.
**No distinction is made in these values between isomers. Thus, fluorocarbon 112 represents both isomers of $C_2Cl_4F_2$, 113 represents both isomers of $C_2Cl_3F_3$ and 114 represents both isomers of $C_2Cl_2F_4$, 115 is $C_2ClF_5$ and 116 is $C_2F_6$.

All runs (1–11) showed a high (90% or better) conversion of fluorocarbon 113 and a low (under 6%, except in run 8) selectivity to fluorocarbon 116. Thus the desired products, fluorocarbons 114 and 115, represented about 90% of the total organics in each instance Runs 1, 5 and 11 all had 0.45–0.46 mol/h fluorocarbon 113 feed, 1.06–1.08 mol/h HF feed, 365° C furnace temperature and 4.42–4.48 sec contact times. A comparison of the results of Runs 1, 5 and 11, which were concluded after 16.5, 54.0 and 101.5 hours of total catalyst utilization shows that 113 conversion remained at about 97% but the selectivity to 115 fell from 60.5% to 55.4% to 54.0%, while the selectivity to 114 rose from 36.5% to 41.6% to 43.4%. The relative consistency in these three runs indicates long catalyst life.

It is contemplated that the reaction products can be distilled at high pressure and low temperature to produce an overhead of HCl and fluorocarbon 116 (b.p. −78.1° C), which overhead can be scrubbed with water to produce fluorocarbon 116. The first bottoms can be flashed once to produce fluorocarbon 115 (bp - 38.7CC) and optionally again to produce fluorocarbon 114 (bp 3.6° C.). The bottoms containing HF and fluorocarbon 113 (bp 47.6° C.) (and optionally also fluorocarbon 114) can be recycled to the reactor. Any fluorocarbon 112 produced by disproportionate of fluorocarbon 113 will be found in the recycle stream.

The examples provided above should not be construe as limiting the invention s defined by the appended claims.

We claim:
1. In a process for the fluorination of a halogenated hydrocarbon of one or two carbons having at least one chlorine atom by reacting said halogenated hydrocarbon with HF in the presence of a chromium(III) oxide or hydroxide catalyst, the improvement wherein the catalyst is the chromium(III) oxide or hydroxide aerogel produced by the process comprising the steps of:
    (a) forming a solution comprising chromium(VI) oxide and a solvent which is reducing to chromium(VI);
    (b) heating said solution to a temperature where said chromium(VI) oxide is reduced by said solvent to a solid oxide or hydroxide form, producing a slurry or gel;
    (c) continuing to heat said slurry or gel under pressure to at least the hypercritical temperature of said solvent; and
    (d) venting said solvent hypercritically to produce a chromium(III) oxide or hydroxide aerogel of surface area at least 400 m$^2$/g, a pore volume of at least about 2 cm$^3$/g and a substantially uniform pore size distribution by mercury porosymmetry.
2. The process of claim 1 wherein said halogenated hydrocarbon is selected from the group consisting of $CCl_3F$, $CCl_2F_2$, $C_2Cl_3F_3$ and $C_2Cl_2F_4$.
3. The process of claim 1 wherein said halogenated hydrogenated is $C_2Cl_3F_3$.

* * * * *